United States Patent [19]
Banks

[11] Patent Number: 5,677,332
[45] Date of Patent: Oct. 14, 1997

[54] ANTIPARASITIC AGENTS

[75] Inventor: Bernard Joseph Banks, Sandwich, United Kingdom

[73] Assignee: Pfizer Inc., New York, N.Y.

[21] Appl. No.: 578,607

[22] PCT Filed: Jul. 8, 1994

[86] PCT No.: PCT/EP94/02297

§ 371 Date: Dec. 22, 1995

§ 102(e) Date: Dec. 22, 1995

[87] PCT Pub. No.: WO95/03317

PCT Pub. Date: Feb. 2, 1995

[30] Foreign Application Priority Data

Jul. 21, 1993 [GB] United Kingdom .................. 9315108

[51] Int. Cl.⁶ .................. A61K 31/335; C07D 315/00
[52] U.S. Cl. .................. 514/450; 514/28; 549/264; 536/7.1
[58] Field of Search .................. 514/450, 32, 28; 549/264, 214; 536/7.1

[56] References Cited

FOREIGN PATENT DOCUMENTS

| 0214731 | 3/1987 | European Pat. Off. . |
| 0285561 | 10/1988 | European Pat. Off. . |
| 9318041 | 9/1993 | WIPO . |

OTHER PUBLICATIONS

Chabala, J. C., J. Med. Chem., 23, 1134–1136, 1980.
Yanai, T., et al., Chemical Abstracts, 113, 13, No. 114954w, 1990.

*Primary Examiner*—Amelia Owens
*Attorney, Agent, or Firm*—Peter C. Richardson; Gregg C. Benson; Robert T. Ronau

[57] ABSTRACT

This invention is directed to novel antiparasitic compounds of formula (I), wherein the broken line represents an optional bond, $R^1$ and $R^4$ being absent when this bond is present, $R^1$, $R^3$, $R^4$ are independently H, OH, halo mercapto, oxo, oximino, or an organic radical, $R^2$ and $R^7$ are organic radicals, $R^6$ is H or an organic radical and $R^{12}$ is OH, halo, $C_1$–$C_8$ alkoxy, $C_1$–$C_9$ alkanoyloxy, or oximino optionally O-substituted by a $C_1$–$C_8$ alkyl, alkenyl, alkynyl, aryl, trialkylsilyl, aralkyl or $C_1$–$C_9$ alkanoyl group.

25 Claims, No Drawings

ANTIPARASITIC AGENTS

This invention relates to antiparasitic agents and in particular to compounds related to the avermectins and milbemycins but having a cyano substituent at the 3-position.

The avermectins am a group of broad-spectrum antiparasitic agents referred to previously as the C-076 compounds. They are produced by fermenting a certain strain of microorganism *Streptomyces avermitilis* in an aqueous nutrient medium. The preparation and structure of these compounds obtained by fermentation are described in British Patent Specification 1573955. The milbemycins are structurally related macrolide antibiotics lacking the sugar residues at the 13-position. They may be produced by fermentation, for example as described in British Patent Specification No. 1390336 and European Patent Specification No. 0170006.

In addition to these fermentation-derived products, a large number of publications describe compounds derived semisynthetically from these products, many of which possess useful antiparasitic properties. Some of this chemistry is reviewed in *Macrolide Antibiotics*, Omura S., Ed., Academic Press, New York (1984) and by Davies, H. G. and Green, R. H. in *Natural Product Reports* (1986), 3, 87–121 and in *Chem. Soc. Rev.* (1991), 20, 211–269 and 271–239.

Compounds related to the original C-076 avermectins have also been prepared by fermentation of avermectin-producing micro-organisms. For example European Patent Specifications 0214731 and 0317148 describe production of compounds related to the C-076 avermectins but having a different substituent at the 25-position by fermentation in the presence, in the fermentation medium, of certain acids.

Other publications mentioning different combinations of substituents at various positions on the avermectin or milbemycin nucleus are EP-A-317148, 340932, 355541, 350187, 410165, 259779 and 254583; DE-A-2329486 and GB-A-2166436.

The avermectins and milbemycins and their derivatives have the structure:

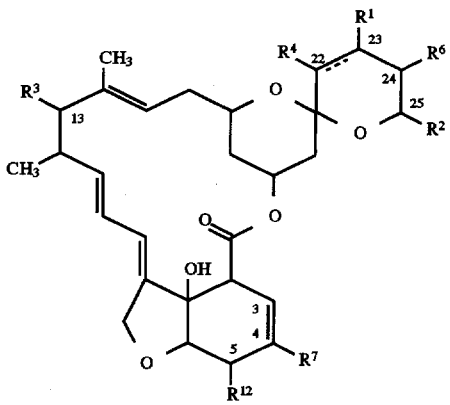

wherein the broken line represents an optional bond, $R^1$ and $R^4$ being absent when this bond is present, $R^1$, $R^3$, $R^4$ and $R^{12}$ are independently H, OH, halo, oxo, oximino or an organic radical, $R^2$ and $R^7$ are organic radicals, and $R^6$ is H or an organic radical.

These compounds include the avermectins themselves and their substituted derivatives in which $R^3$ is a 4'-(α-L-oleandrosyl)-α-L-oleandrosyloxy group, optionally substituted at the 4" position; the avermectin monosaccharides and their derivatives in which $R^3$ is α-L-oleandrosyloxy, optionally substituted at the 4' position; the avermectin aglycones and their derivatives in which $R^3$ is OH or a substituent other than oleandrosyl replacing this group; and the milbemycins and their derivatives in which $R^3$ is H.

All the avermectins and structurally related milbemycins and their derivatives hitherto reported do not have a substituent at the 3-position when the double bond is in the C3–C4 position, neither has any process capable of producing such compounds been reported.

It has now been discovered that avermectin and milbemycin derivatives having a cyano substituent at the 3-position may be prepared and that some of these compounds have outstanding antiparasitic properties.

Compounds of the invention are of formula (I):

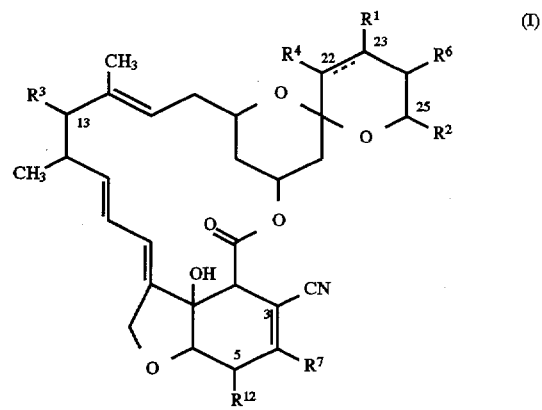

wherein the broken line represents an optional bond, $R^1$ and $R^4$ being absent when this bond is present, $R^1$, $R^3$, $R^4$ are independently H, OH, halo, oxo, oximino, or an organic radical, $R^2$ and $R^7$ are organic radicals, $R^6$ is H or an organic radical and $R^{12}$ is OH, halo, $C_1$–$C_8$ alkoxy, $C_1$–$C_9$ alkanoyloxy, or oximino optionally O-substituted by a $C_1$–$C_8$ alkyl, alkenyl, alkynyl, aryl, trialkylsilyl, aralkyl or $C_1$–$C_9$ alkanoyl group.

Compounds according to the invention include those in which the 22–23 optional bond is present and those in which this optional bond is absent (i.e. a single bond between the 22 and 23 positions); $R^1$ is H, OH, $C_1$–$C_8$ alkoxy optionally substituted by halo or by $C_1$–$C_4$ alkoxy, $C_2$–$C_5$ alkanoyl, $C_2$–$C_5$ alkoxy carbonyl, carboxy, mercapto or by aryl, or $R^1$ is $C_3$–$C_8$ alkenyloxy, $C_2$–$C_9$ alkylcarbonyloxy or $C_3$–$C_9$ alkenylcarbonyloxy, arylcarbonyl or carbamoyl optionally substituted by a $C_1$–$C_9$ alkyl group, or $R^1$ is attached to the remainder of the molecule by a double bond and is oxo or oximino optionally O-substituted by a $C_1$–$C_8$ alkyl, alkenyl, alkynyl, trialkylsilyl, aryl or aralkyl group, or is methylene optionally substituted by a cyano or $C_1$–$C_9$ alkyl group;

$R^4$ is H, OH or $C_1$–$C_8$ alkoxy or $C_1$–$C_9$ alkanoyloxy, or is attached to the remainder of the molecule by a double bond and is =$CH_2$, oxo or oximino optionally substituted as above;

$R^2$ is
(a) an alpha-branched $C_1$–$C_8$ alkyl, alkenyl (including but-2-enyl, pent-2-enyl, and 4-methylpent-2-enyl), alkoxy-alkyl, or alkylthioalkyl group; an alpha-branched $C_4$–$C_8$ alkynyl group; a ($C_4$–$C_8$) cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^8$ wherein $R^8$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or partially unsaturated and which may optionally be substituted by one or more $C_1$–$C_4$ alkyl groups or halo atoms; or a group of the formula $SR^9$ wherein $R^9$ is $C_1$–$C_8$ alkyl, $C_2$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur containing heterocylic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$)alkoxy-carbonyl group, said substituents on $R_2$ being attached to either or both of a terminal carbon atom and a carbon atom adjacent a terminal carbon atom of $R^2$; or (d) =$CH_2$ or a group of the formula:

wherein $R^{10}$ and $R^{11}$ are both H; $R^{10}$ is H and $R^{11}$ is $C_1$–$C_3$ alkyl, or one of $R^{10}$ and $R^{11}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy($C_1$–$C_4$)alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di($C_1$–$C_4$) alkylamino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkylthio groups, halo atoms, trifluoromethyl, and cyano;

or $R^2$ may be a group of formula (II):

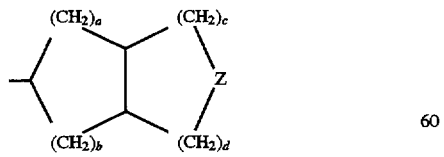

wherein Z is O, S or —$CH_2$— and a, b, c and d may each independently be 0, 1 or 2; the sum of a, b, c, and d not exceeding 5;

$R^3$ is hydrogen, hydroxy, $C_1$–$C_8$ alkoxy or alkenoxy, $C_1$–$C_9$ alkanoyloxy or alkenoyloxy, aroyloxy, oxymethyleneoxy-($C_1$–$C_5$)alkyloxy-($C_1$–$C_5$) alkyl, halogen, oxo, or optionally substituted oximino, hydrazono, carbazido or semicarbazido, N-($C_1$–$C_4$)alkyl semicarbazido, N,N-di($C_1$–$C_4$) alkylsemicarbazido, $C_1$–$C_5$ alkanoylhydrazido, benzoylhydrazido or ($C_1$–$C_4$)alkyl benzoylhydrazido; or $R_3$ is

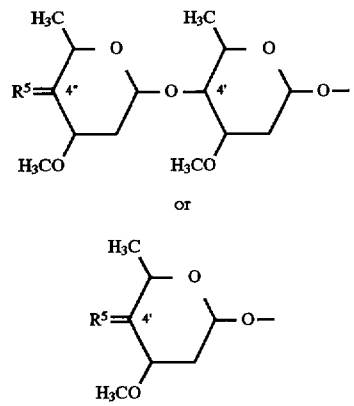

wherein $R^5$ is attached to C-4" or C-4' by a single bond and is hydrogen, halo, hydroxy, $C_1$–$C_9$ alkanoyloxy or alkenoyloxy, aroyloxy, $C_1$–$C_8$ alkoxy, amino, N-($C_1$–$C_8$)alkylamino, N,N-di ($C_1$–$C_9$)alkylamino, N-($C_1$–$C_5$)alkanoylamino, or N,N-di($C_1$–$C_9$)alkanoylamino;

or $R^5$ is attached to C-4" or C-4' by a double bond and is oxo, optionally substituted oximino, semicarbazido, N-($C_1$–$C_4$)alkylsemicarbazido, N,N-di($C_1$–$C_4$)alkylsemicarbazido, ($C_1$–$C_5$) alkanoylhydrazido, benzoylhydrazido, or ($C_1$–$C_4$) alkylbenzoylhydrazido;

$R_6$ is H or $C_1$–$C_6$ alkyl;

and $R_7$ is methyl, hydroxymethyl, ($C_1$–$C_4$ alkoxy)- methyl, ($C_2$–$C_5$ alkanoyl)oxymethyl,($C_2$–$C_5$ alkenoyl)-oxymethyl, aroyloxymethyl, aralkanoyloxymethyl, oxo, optionally substituted oximino, halomethyl, azidomethyl or cyanomethyl.

Compounds of the invention include those in which $R^1$ is H, OH, O-($C_1$–$C_4$)alkyl, O-($C_1$–$C_5$)alkanoyl, oxo and oximino optionally substituted by $C_1$–$C_4$ alkyl or aryl ($C_1$–$C_4$)alkyl; those in which $R^2$ is straight or branched-chain alkyl, alkenyl, cycloalkyl or cycloalkenyl (including methyl, ethyl, 2-propyl, 2-butyl, 2-buten-2-yl, 2-penten-2-yl, 4-methyl-2-penten-2-yl and cyclohexyl); those in which $R^4$ is H, OH, oxo or oximino; and those in which $R^3$ is H or is of formula

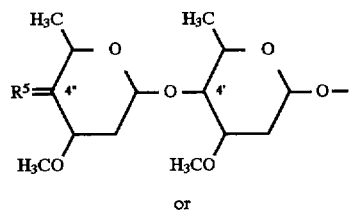

or

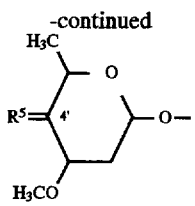

where $R^5$ is OH, $(C_1-C_4)$alkoxy, $(C_2-C_5)$alkanoyloxy, amino, N-$(C_1-C_4)$alkylamino, N-$(C_1-C_5)$alkanoylamino, oxo or oximino optionally substituted by a $C_1-C_4$ alkyl group; and those in which $R^{12}$ is OH, oximino or methoxy.

In all the above definitions, unless the context requires otherwise, alkyl groups containing 3 or more carbon atoms may be straight or branched-chain; halo means fluoro, chloro, bromo or iodo; and aryl means phenyl optionally substituted by one or more $C_1-C_4$ alkyl or $C_1-C_4$ alkoxy groups or halo atoms.

The avermectins and monosaccharides are generally preferred over the aglycones and milbemycins and their derivatives having no saccharide groups at the 13-position.

Particular compounds within the scope of the invention are described in the Examples.

It will be understood that the compounds of the invention include several asymmetric centres and accordingly may exist as several pairs of stereoisomers. The invention includes all such stereoisomers, whether separated or not.

The compounds of the invention in which $R^{12}$ is OH may be prepared from known avermectin or milbemycin derivatives as shown in the following reaction scheme:

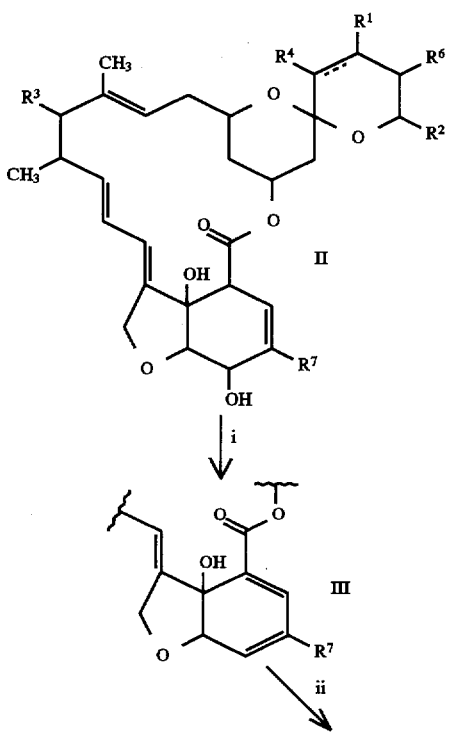

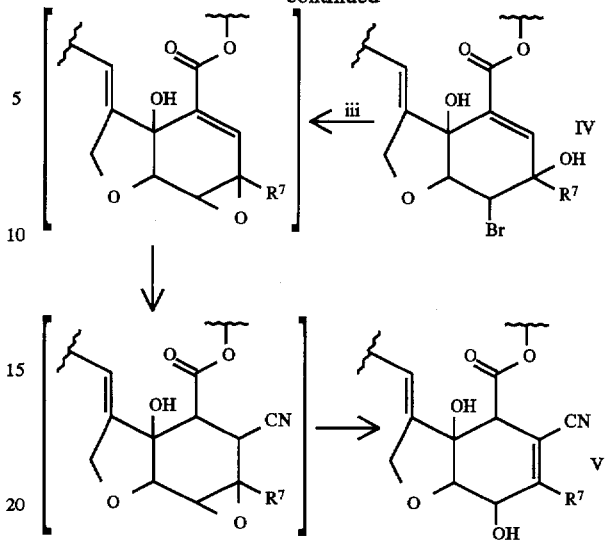

Reagents:- i.a. Triphenylphosphine/Diethylazodicarboxylate/
4-Nitrophenol/Tetrahydrofuran  b. Diazabicycloundecane/
Tetrahydrofuran ii. N-Bromoacetamide/Tetrahydrofuran/Water iii. Lithium Cyanide/Dimethylformamide In this method compound (II) in which $R^1-R^4$ and $R^6$, $R^7$ are as defined above is converted to the corresponding 2-3 and 4-5 diene (III), for example by reaction with triphenylphosphine and diethylazodicarboxylate in the presence of 4-nitrophenol in a solvent such as tetrahydrofuran, followed by treatment with diazabicycloundecane in tetrahydrofuran (step (i)). The diene (III) may be separated from the reaction mixture and purified by conventional methods. The diene may then be converted to the corresponding 5-bromo-4-hydroxy derivative (IV) by treatment with N-bromoacetamide and water in an inert, water-miscible solvent such as tetrahydrofuran (step (ii)). After separation and purification compound (IV) may then be allowed to react with an ionic cyanide such as lithium cyanide in a polar-solvent such as dimethylformamide in step (iii) to yield the desired compound (V); the reaction is believed to proceed through the intermediate compounds shown in brackets.

In the above-described synthesis the bromine of compound (IV) may be replaced by other halogens. For example N-chloro or N-iodo succinimide may be used instead of N-bromoacetamide to produce the corresponding 5-chloro or 5-iodo analogue of compound (IV), which may be converted to a compound of formula (V) by the same method.

The compounds of formula (I) in which $R^{12}$ is OH may be converted to other derivatives by conventional synthetic steps. For example they may be treated with an alkyl halide and silver oxide to prepare the 5-alkoxy derivative, or treated with manganese dioxide to produce the corresponding 5-oxo compound which in turn may be treated with hydroxylamine to give the 5-oximino compound.

The starting materials of formula (II) comprising different combinations of substituents $R^1-R^7$, may generally be made by methods known in the art and discussed in the above-mentioned publications. It is believed that the above-described method of the invention is applicable to all starting compounds of formula (II) in which substituents $R^1-R^7$ are compatible with the reagents used. However in some instances it may be necessary or desirable to replace some of the $R^1$–$R^7$ substituents with other substituents after conversion of the formula (II) starting material to the 3-cyano compound. Such conversions, together with any required conversions of the $R^{12}$ group from hydroxy to other radicals, may also be carried out by methods known in the art and as described in the published patent documents and other documents herein mentioned.

The compounds of the invention are highly active antiparasitic agents. Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect animals and humans including gastro-intestinal parasites such as Ancylostoma, Necator, Ascaris, Strongyloides, Trichinella, Toxocara, Capillaria, Trichuris, Enterobius and parasites which are found in the blood or other tissues and organs such as filarial worms and the extra-intestinal stages of Strongyloides, Trichinella and Toxocara.

The compounds are also of value in treating ectoparasite infections including in particular arthropod ectoparasites of humans, animals and birds such as ticks, mites, lice, fleas, blowfly, biting insects and migrating dipterous larvae which can affect cattle and horses.

The compounds of formula (I) may be administered as a formulation appropriate to the specific use envisaged and to the particular species of host animal being treated and the parasite or insect involved. For use as an anthelmintic the compounds may be administered by injection, either subcutaneously or intramuscularly, alternatively they may be administered orally in the form of a capsule, bolus, tablet, chewable tablet or liquid drench, or they may be administered as a topical formulation or as an implant. For topical application dip, spray, powder, dust, pour-on, spot-on, jetting fluid, shampoos, collar, tag or harness may be used. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. Pour-on or spot-on formulations may be prepared by dissolving the active ingredient in an acceptable liquid carder vehicle, such as butyl digol, liquid paraffin or non-volatile ester with or without addition of a volatile component such as isopropanol. Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and the body weight of the host. The compounds may be administered continuously, particularly for prophylaxis, by known methods. Generally for oral, parenteral and pour-on administration a dose of from about 0.001 to 10 mg per kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing-with the normal animal feed.

For use as an insecticide and for treating agricultural pests the compounds are applied as sprays, dusts, pour-on formulations, emulsions and the like in accordance with standard agricultural practice.

For human use the compounds are administered as a pharmaceutically acceptable formulation in accordance with normal medical practice.

The compounds are also useful against insect pests of stored grains such as Tribolium sp., Tenebrio sp., and of agricultural plants such as spider mites, (Tetranychus sp.) aphids, (Acyrthiosiphon sp.), against migratory orthopterans such as locusts and immature stages of insects living on plant tissue. The compounds am useful as nematocides for the control of soil nematodes and plant parasites such as Meloidogyne sp. which may be of importance in agriculture. The compounds are active against other plant pests such as the southern army worm and Mexican bean beetle larvae.

For use as insecticides the compounds are applied as sprays, dusts, emulsions, pour-on formulation and the like in accordance with standard veterinary practice.

The invention is illustrated by the following Examples, in which "avermectin B2" refers to an avermectin having an OH substituents at the 5- and 23-position and a single bond at the 22–23 position, "avermectin B1" refers to an avermectin having a double bond at the 22–23 position and an OH substituent at the 5-position, and "avermectin A1" is as for avermectin B1 but having a methoxy group at the 5-position.

EXAMPLE 1

5-Bromo-5-deoxy-4-hydroxy-$\Delta^{2,3}$-22,23-dihydro-25-cyclohexylavermectin B1 monosaccharide (A compound of formula (IV) in the foregoing reaction scheme)

To a solution of 5-deoxy-3,4,22,23-tetrahydro-$\Delta^{2,3;4,5}$-25-cyclohexylavermectin B1 monosaccharide from Preparation 2 (3.8 g) in tetrahydrofuran (90 ml) and water (10 ml) at room temperature was added over a period of forty minutes a solution of N-bromoacetamide (0.708 g) in tetrahydrofuran (2 ml). The mixture was stirred for 16 hours then N-bromoacetamide (0.35 g) in tetrahydrofuran (1 ml) was added and the mixture stirred for 2 hours. Further N-bromoacetamide (0.4 g) in tetrahydrofuran (1.2 ml) was added and the mixture stirred for a further 2 hours. The reaction mixture was then partitioned between ether and saturated aqueous sodium chloride solution. After drying ($Na_2SO_4$) and evaporation a yellow oil (5 g) was obtained. This was purified by reverse-phase high performance liquid-chromatography using methanol:water (90:10) as eluent. Combination and evaporation of appropriate fraction gave a white solid (0.9 g) which was further purified by reverse-phase high performance liquid chromatography on a 2" diameter Dynamax (trade mark) ODS C-18 column eluted with acetonitrile:methanol:water (65:20:15). Combination and evaporation of appropriate fractions gave the title compound as an amorphous white powder which was characterised by its nmr and mass spectra.

EXAMPLES 2 and 3

3-Cyano-25-cyclohexyl-22,23-dihydroavermectin B1 monosaccharide
and
3-Cyano-5-deoxy-4,5-epoxy-25-cyclohexyl-22,23-dihydroavermectin B1 monosaccharide To a solution of 5-bromo-5-deoxy-4-hydroxy-$\Delta^{2,3}$-22,23-dihydroavermectin B1 monosaccharide from Example 1 (2.57 g) in dimethylformamide (600 ml) was added lithium cyanide in dimethylformamide (6.4 ml, 0.5M). The mixture was stirred at room temperature for 2.5 hours then partitioned between water and ether. The organic layer was separated and washed with water. The combined aqueous layers were extracted with ether. The combined ether extracts were dried ($Na_2SO_4$) and evaporated. The resulting oil was taken up in ether and washed with water. The ether layer was separated, dried ($Na_2SO_4$) and evaporated to yield a yellow oil (3.5 g) which was purified in three equal batches by reverse-phase high performance liquid chromatography on a 2" diameter Dynamax (trade mark) ODS C18 column eluted initially with acetonitrile:methanol:water (72:13:15) at 45 ml/min. for 60 minutes. The methanol content was then increased by 1% every 4 minutes until all materials had eluted.

Combination and evaporation of appropriate fractions gave 3-cyano-25-cyclohexyl-22,23-dihydroavermectin B1 monosaccharide and the intermediate compound, 3-cyano-5-deoxy-4,5-epoxy-25-cyclohexyl-22,23-dihydroavermectin B1 monosaccharide as amorphous white powders which were characterised by their nmr and mass spectra.

EXAMPLE 4

3-Cyano-5-oximino-25-cyclohexyl-22,23-dihydroavermectin B1 monosaccharide

To a solution of 3-cyano-25-cyclohexyl-22,23-dihydroavermectin B1 monosaccharide from Example 2 (36 mg) in ether (1 ml) was added manganese dioxide (15 mg). The reaction mixture was stirred at room temperature and monitored by thin layer chromatography ($SiO_2$ eluted with 5% methanol in dichloromethane) for disappearance of starting material. Further quantities of manganese dioxide were added and stirring continued until all the starting material was consumed. The resulting mixture was diluted with ether (10 ml) and filtered through Hyflo (trade mark). The filtrate was evaporated and the residue taken up in ether (1 ml). Hydroxyammonium chloride (26 mg) and pyridine (1 ml) were added. The reaction mixture was maintained at room temperature for one hour then partitioned between ether and aqueous citric acid solution. The ether layer was separated, dried ($Na_2SO_4$) and evaporated. The white solid so obtained was purified by reverse-phase high performance liquid chromatography on a 1" diameter Dynamax (trade mark) ODS C18 column eluted with methanol:water (86.14). Combination and evaporation of appropriate fractions gave the title compound as an amorphous white solid which was characterised by its nmr and mass spectra.

EXAMPLES 5 and 6

3-Cyano-25-cyclohexyl-22,23-dihydroavermectin A1 monosaccharide
and
4'-O-Methyl-3-cyano-25-cyclohexyl-22,23-dihydroavermectin A1 monosaccharide A solution of 3-cyano-25-cyclohexyl-22,23-dihydroavermectin B1 monosaccharide from Example 2 (90 mg) in ether (5 ml) and methyl iodide (1.25 ml) containing a suspension of silver oxide (360 mg) was stirred vigorously for 2 hours, then filtered and evaporated. The product was purified by reverse-phase high performance liquid chromatography on a 1" diameter Dynamax (trade mark) ODS C18 column eluted with methanol:water (80:20→100:0) over two hours. Combination and evaporation of appropriate fractions gave 3-cyano-25-cyclohexyl-22,23-dihydroavermectin A1 monosaccharide and 4'-O-methyl-3-cyano-25-cyclohexyl-22,23-dihydro-avermectin A1 monosaccharide as amorphous white powders which were characterised by their nmr and mass spectra.

EXAMPLE 7

5-Bromo-5-deoxy-4-hydroxy-$\Delta^{2,3}$-25-cyclohexylavermectin B2

(A compound of formula (IV) in the foregoing reaction scheme)

To a stirred solution of 5-deoxy-3,4-dihydro-$\Delta^{2,3;4,5}$-25-cyclohexylavermectin B2 (Preparation 3) (2 g) in tetrahydrofuran (22.5 ml) and water (2.5 ml) was added N-bromoacetamide (0.45 g), portionwise, over a period of 1 hour. Stirring was continued for a further 30 minutes. The reaction mixture was poured into ether (100 ml) and extracted with water (100 ml). The organic layer was separated, dried ($MgSO_4$) and evaporated. The crude product was purified in two equal portions by reverse-phase high performance liquid chromatography on a 2" diameter Dynamax (trade mark) ODS C18 column eluted with methanol:water (82:18). Combination and evaporation of appropriate fractions gave the title compound (280 mg) as an amorphous white powder which was characterised by its nmr and mass spectra.

EXAMPLE 8

3-Cyano-25-cyclohexylavermectin B2

To a solution of 5-bromo-5-deoxy-4-hydroxy-$\Delta^{2,3}$-25-cyclohexyl-avermectin B2 from Example 7 (280 mg) in dimethylformamide (9 ml) was added lithium cyanide in dimethylformamide (1 ml, 0.5M). After 1.5 hours at room temperature the reaction mixture was diluted with ether (100 ml) and extracted with water (100 ml). The aqueous layer was separated and extracted with ether (100 ml). The combined organic layers were washed with saturated aqueous sodium chloride solution, dried ($MgSO_4$) and evaporated. The crude product was purified by reverse-phase high performance liquid chromatography on a 2'-diameter Dynamax (trade mark) ODS C18 column eluted with water-:methanol (20,80). Combination and evaporation of appropriate fractions gave the title compound as an amorphous white powder which was characterised by its nmr and mass spectra.

PREPARATION 1

22,23-Dihydro-25-cyclohexylavermectin B1 monosaccharide

25-Cyclohexylavermectin B1 (from EP-A-214731) (9.9 g) was dissolved in toluene (1 liter) and Wilkinson's catalyst (tristriphenylphosphine rhodium (I) chloride) (9.25 g) was added. The solution was hydrogenated on a large Parr shaker at room temperature at 50 psi hydrogen pressure. After 3 hours the reaction vessel was depressurised and allowed to stand for 12 hours before addition of a further portion of catalyst (5 g) and hydrogenated as before for a further 2 hours after which no starting material remained. The solution was filtered, evaporated to dryness under vacuum and the residue chromatographed on silica eluting with methylene chloride then methylene chloride:methanol 9:1.

The crude product was then chromatographed again on silica (200 g) eluting with methylene chloride:methanol 19:1 to give after evaporation of the solvent under vacuum impure 22,23-dihydro-25-cyclohexylavermectin B1 as a brown foam (10 g). This material was dissolved in a mixture of isopropanol (200 ml) and sulphuric acid (2 ml) and the brown solution was stirred at room temperature for 15 hours then poured into a mixture of ice and water (500 ml) and extracted with methylene chloride (3×200 ml). The organic layer was washed with saturated potassium hydrogen carbonate solution (100 ml), water (2×50 ml) dried over anhydrous magnesium sulphate and evaporated under vacuum to give a crude gum which was chromatographed on silica eluting with methylene chloride then methylene chloride-:ethyl acetate 2:1 to give the title compound (8.2 g). Mass and nmr spectra were fully consistent with the proposed structure.

PREPARATION 2

5-Deoxy-3,4,22,23-tetrahydro-$\Delta^{2,3;4,5}$-25-cyclohexylavermectin B1 monosaccharide (A compound of formula (III) in the foregoing scheme)

To a stirred solution of 22,23-dihydro-25-cyclohexylavermectin B1 monosaccharide (5.00 g), triphenylphosphine (3.46 g) and 4-nitrophenol (0.92 g) in anhydrous tetrahydrofuran (50 ml) at 0° C. was added diethylazodicarboxylate (2.3 ml). After 30 minutes triphenylphosphine (1.6 g) and diethylazodicarboxylate (2.0 ml) was added and stirring continued for a further 30 minutes during which time the reaction mixture was allowed to warm to room temperature. 1,8-Diazobicylo[5.4.0]undec-7-ene (8 ml) was added in four equal portions over 30 minutes and the mixture then diluted with ether (500 ml). The mixture was washed with aqueous citric acid (250 ml, ×2), sodium hydroxide (250 ml, 2N, ×2) and brine (250 ml, ×2). Each aqueous layer was extracted with ether (200 ml). The combined organic layers were washed with brine (250 ml), dried (Na$_2$SO$_4$) and evaporated. The residue was purified by column chromatography on silica gel (100 g) eluted with hexane:ether—1:1 to 1:3. Combination and evaporation of appropriate fractions gave the title compound (1.78 g) as a pale yellow solid which was characterised by mass and nmr spectroscopy.

PREPARATION 3

5-Deoxy-3,4-dihydro-$\Delta^{2,3;4,5}$-25-cyclohexylavermectin B2

(A compound of formula (III) in the foregoing reaction scheme)

5-Deoxy-3,4-dihydro-$\Delta^{2,3;4,5}$-25-cyclohexylavermectin B2 was prepared analogously from 25-cyclohexylavermectin B2 (EP-A-214731) by the method given for Preparation 2.

I claim:
1. A compound of the formula (I):

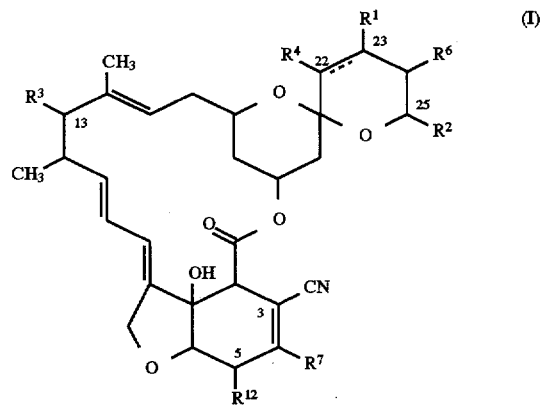

wherein the broken line represents an optional bond, $R^1$ and $R^4$ being absent when this bond is present;

$R^1$ is H, OH, $C_1$–$C_8$ alkoxy optionally substituted by halo or by $C_1$–$C_4$ alkoxy, $C_2$–$C_5$ alkanoyl, $C_2$–$C_5$ alkoxycarbonyl, carboxy, mercapto or by aryl; $C_3$–$C_8$ alkenyloxy, $C_2$–$C_9$ alkylcarbonyloxy, $C_3$–$C_9$ alkenylcarbonyloxy, arylcarbonyl or carbamoyl optionally substituted by a $C_1$–$C_9$ alkyl group, or $R^1$ is attached to the remainder of the molecule by a double bond and is oxo or oximino optionally O-substituted by $C_1$–$C_8$ alkyl, $C_1$–$C_8$ alkenyl, $C_1$–$C_8$ alkynyl, trialkylsilyl, aryl or aralkyl; or methylene optionally substituted by cyano or $C_1$–$C_9$ alkyl;

$R^2$ is (a) a straight or branched $C_3$–$C_8$ alkyl, alkenyl, alkoxyalkyl, or alkylthioalkyl group; an alpha-branched $C_4$–$C_8$ alkynyl group; a ($C_4$–$C_8$)cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —CH$_2$R$^8$ wherein R$^8$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3$–$C_8$ cycloalkyl or $C_5$–$C_8$ cycloalkenyl group, either or which may optionally be substituted by methylene or one or more $C_1$–$C_4$ alkyl groups or halo atoms; or a 3 to 6 membered oxygen or sulphur containing heterocyclic ring which may be saturated, or partially unsaturated and which may optionally be substituted by one or more $C_1$–$C_4$ alkyl groups or halo atoms; or a group of the formula SR$^9$ wherein R$^9$ is $C_1$–$C_8$ alkyl, $C_2$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur-containing heterocyclic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$) alkoxy-carbonyl group, said substituents on $R_2$ being attached to either or both of a terminal carbon atom and a carbon atom adjacent a terminal carbon atom of $R^2$; or (d) =$CH_2$ or a group of the formula

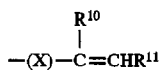

wherein $R^{10}$ and $R^{11}$ are both H; $R^{10}$ is H and $R^{11}$ is $C_1$–$C_3$ alkyl, or one of $R^{10}$ and $R^{11}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy ($C_1$–$C_4$)alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di($C_1$–$C_4$)alkylamino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkylthio groups, halo atoms, trifluoromethyl, and cyano;

or $R^2$ may be a group of formula (II):

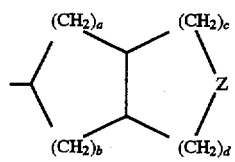

wherein Z is O, S or —$CH_2$— and a, b, c and d may each independently be 0, 1 or 2; the sum of a, b, c, and d not exceeding 5;

$R^3$ is hydrogen, hydroxy, $C_1$–$C_8$ alkoxy, $C_1$–$C_8$ alkenoxy, $C_1$–$C_9$ alkanoyloxy, $C_1$–$C_9$ alkenoyloxy, aroyloxy, oxymethyleneoxy-($C_1$–$C_5$)alkyloxy-(C$_1$–$C_5$)alkyl, halogen, oxo, or optionally substituted oximino, hydrazono, carbazido or semicarbazido, N-($C_1$–$C_4$)alkyl semicarbazido, N,N-di-($C_1$–$C_4$)alkyl semicarbazido, $C_1$–$C_5$ alkanoylhydrazido, benzoylhydrazido or $C_1$–$C_4$ alkylbenzoylhydrazido; or $R^3$ is

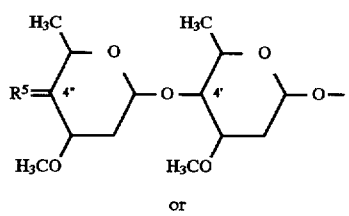

or

—continued

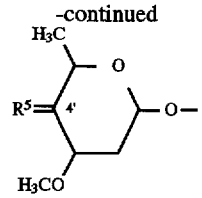

$R^4$ is H, OH, $C_1$–$C_8$ alkoxy or $C_1$–$C_9$ alkanoyloxy, or is attached to the remainder of the molecule by a double bond and is oxo or oximino optionally substituted by $C_1$–$C_8$ alkyl, $C_1$–$C_8$ alkenyl, $C_1$–$C_8$ alkynyl, trialkylsilyl, aryl or aralkyl; or methylene optionally substituted by cyano or $C_1$–$C_9$ alkyl;

$R^5$ is attached to C-4" or C-4' by a single bond and is hydrogen, halo, hydroxy, $C_1$–$C_9$ alkanoyloxy or alkenoyloxy, aroyloxy, $C_1$–$C_8$ alkoxy, amino, N-($C_1$–$C_8$)alkylamino, N,N-di($C_1$–$C_9$)alkylamino, N-($C_1$–$C_5$)alkanoylamino, or N,N-di($C_1$–$C_9$) alkanoylamino; or $R^5$ is attached to C-4" or C-4' by a double bond and is oxo, optionally substituted oximino, semicarbazido, N-($C_1$–$C_4$)alkylsemicarbazido, N,N-di($C_1$–$C_4$) alkylsemicarbazido, ($C_1$–$C_5$)alkanoylhydrazido, benzoylhydrazido, or ($C_1$–$C_4$) alkylbenzoylhydrazido;

$R^6$ is H or $C_1$–$C_6$ alkyl;

$R^7$ is methyl, hydroxymethyl, ($C_1$–$C_4$ alkoxy)-methyl, ($C_2$–$C_5$)alkanoyl)oxymethyl, ($C_2$–$C_5$)alkenoyl) oxymethyl, aroyloxymethyl, aralkanoyloxymethyl, oxo, optionally substituted oximino, halomethyl, azidomethyl or cyanomethyl;

and $R^{12}$ is OH, halo, $C_1$–$C_8$ alkoxy, $C_1$–$C_9$ alkanoyloxy, or oximino optionally O-substituted by a $C_1$–$C_8$ alkyl, alkenyl, alkynyl, aryl, trialkylsilyl, aralkyl or $C_1$–$C_9$ alkanoyl group.

2. A compound of claim 1, where the double bond is absent and $R^1$ is H, OH, $C_1$–$C_8$ alkoxy optionally substituted by halo or by $C_1$–$C_4$ alkoxy, $C_2$–$C_5$ alkanoyl, $C_2$–$C_5$ alkoxycarbonyl, carboxy, mercapto or by aryl, or $R^1$ is $C_3$–$C_8$ alkenyloxy, $C_1$–$C_9$ alkanoyloxy or $C_3$–$C_9$ alkenylcarbonyloxy, arylcarbonyl or carbamoyl optionally substituted by a $C_1$–$C_9$ alkyl group, or $R^1$ is attached to the remainder of the molecule by a double bond and is oxo or oximino optionally O-substituted by a $C_1$–$C_8$ alkyl, alkenyl, alkynyl, trialkylsilyl, aryl or aryl-($C_1$–$C_4$)-alkyl group, or is methylene optionally substituted by a cyano or $C_1$–$C_9$ alkyl group or $R^1$ and $R^4$ are absent and the double bond is present.

3. A compound of claim 1, where $R^4$ is H, OH, or $C_1$–$C_8$ alkoxy or $C_1$–$C_9$ alkanoyloxy, or is attached to the remainder of the molecule by a double bond and is =$CH_2$, oxo or optionally O-substituted oximino.

4. A compound of claim 1, where $R^2$ is (a) a straight or branched $C_3$–$C_8$ alkyl, alkenyl, alkoxyalkyl, or alkylthioalkyl group; an alpha-branched $C_4$–$C_8$ alkynyl group; a ($C_4$–$C_8$)cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^8$ wherein $R^8$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_3$–$C_8$ cycloalkyl or $C_5$–$C_8$ cycloalkenyl group, either or which may optionally be substituted by methylene or one or more $C_1$–$C_4$ alkyl groups or halo atoms; or a 3 to 6 membered oxygen or sulphur containing heterocyclic ring which may be saturated, or partially unsaturated and which may optionally be substituted by one or more $C_1$–$C_4$ alkyl groups or halo atoms; or a group of the formula $SR^9$ wherein $R^9$ is $C_1$–$C_8$ alkyl, $C_2$–$C_8$ alkenyl, $C_3$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur-containing heterocyclic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$) alkoxy-carbonyl group, said substituents on $R_2$ being attached to either or both of a terminal carbon atom and a carbon atom adjacent a terminal carbon atom of $R^2$; or (d) =$CH_2$ or a group of the formula $$-(X)-\underset{\underset{R^{10}}{|}}{C}=CHR^{11}$$

wherein $R^{10}$ and $R^{11}$ are both H; $R^{10}$ is H and $R^{11}$ is $C_1$–$C_3$ alkyl, or one of $R^{10}$ and $R^{11}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy($C_1$–$C_4$)alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di($C_1$–$C_4$) alkylamino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkylthio groups, halo atoms, trifluoromethyl, and cyano;

or $R^2$ may be a group of formula (II):

<img> wherein Z is O, S or —$CH_2$— and a, b, c and d may each independently be 0, 1 or 2; the sum of a, b, c, and d not exceeding 5.

5. A compound of claim 1, where $R^3$ is hydrogen, hydroxy, $C_1$–$C_8$ alkoxy or alkenoxy, $C_1$–$C_9$ alkanoyloxy or alkenoyloxy, aroyloxy, oxymethyleneoxy-($C_1$–$C_5$) alkyloxy-($C_1$–$C_5$)alkyl, halogen, oxo, or optionally substituted oximino, hydrazono, carbazido or semicarbazido, N-($C_1$–$C_4$)alkyl semicarbazido, N,N-di($C_1$–$C_4$) alkylsemicarbazido, $C_1$–$C_5$ alkanoylhydrazido, benzoylhydrazido or ($C_1$–$C_4$)alkyl benzoylhydrazido; or $R_3$ is <img> or

<img> wherein $R^5$ is attached to C-4" or C-4' by a single bond and is hydrogen, halo, hydroxy, $C_1$–$C_9$ alkanoyloxy or alkenoyloxy, aroyloxy, $C_1$–$C_8$ alkoxy, amino, N-($C_1$–$C_8$) alkylamino, N,N-di($C_1$–$C_9$)alkylamino, N-($C_1$–$C_5$) (alkanoylamino, or N,N-di($C_1$–$C_9$)alkanoylamino; or $R^5$ is attached to C-4" or C-4' by a double bond and is oxo, optionally substituted oximino, semicarbazido, N-($C_1$–$C_4$)alkylsemicarbazido, N,N-di($C_1$–$C_4$) alkylsemicarbazido, ($C_1$–$C_5$)alkanoylhydrazido, benzoylhydrazido, or ($C_1$–$C_4$)alkylbenzoylhydrazido.

6. A compound of claim 1, where $R_6$ is H or $C_1$–$C_6$ alkyl.

7. A compound of claim 1, where $R_7$ is methyl, hydroxymethyl, ($C_1$–$C_4$ alkoxy)-methyl, ($C_2$–$C_5$ alkanoyl) oxymethyl, ($C_2$–$C_4$ alkenoyl)-oxymethyl, aroyloxymethyl, aralkanoyloxymethyl, oxo, optionally substituted oximino, halomethyl, azidomethyl or cyanomethyl.

8. A compound of claim 4 where $R^2$ is an alkyl or cycloalkyl group.

9. A compound according to claim 8, where $R^2$ is cyclohexyl, sec-butyl or isopropyl.

10. A compound of claim 7, where $R^7$ is methyl and the optional 22–23 bond is present or this optional bond is absent and $R^1$ is H or OH.

11. A compound according to claim 8 where $R^4$ is H.

12. A compound according to claim 1, where $R^{12}$ is OH, chloro, fluoro, methoxy, acetoxy, oximino or methoximino.

13. A compound according to claim 12 where $R^{12}$ is OH or oximino.

14. 3-cyano-25-cyclohexyl-22,23-dihydroavermectin B1 monosaccharide.

15. 3-cyano-5-oximino-25-cyclohexyl-22,23-dihydroavermectin B1 monosaccharide.

16. 3-cyano-25-cyclohexyl-22,23-dihydroavermectin A1 monosaccharide.

17. 4'-O-methyl-3-cyano-25-cyclohexyl-22,23-dihydroavermectin A1 monosaccharide.

18. 3-cyano-25-cyclohexylavermectin B2.

19. 5-Bromo-5-deoxy-4-hydroxy-$\Delta^{2,3}$-22,23-dihydro-25-cyclohexylavermectin B1 monosaccharide.

20. 3-cyano-5-deoxy-4,5-epoxy-25-cyclohexyl-22,23-dihydroavermectin B1 monosaccharide.

21. 5-bromo-5-deoxy-4-hydroxy-$\Delta^{2,3}$-25-cyclohexylavermectin B2.

22. A pharmaceutical composition comprising an antiparasitic effective amount of a compound of claim 1 and a pharmaceutically acceptable carrier or excipient.

23. A veterinary composition comprising an antiparasitic effective amount of a compound of claim 1 and a pharmaceutically acceptable carrier or diluent.

24. A method of treating a parasitic infestation in a mammal suffering from a parasitic infestation comprising administering to said mammal a parasitic infestation treating effective amount of a compound of claim 1.

25. A method of preventing infestation of a mammal by a parasite comprising administering to said mammal an amount of a compound of claim 1 sufficient to prevent said infestation by said parasite in said mammal.

* * * * *